United States Patent
Valaie

(10) Patent No.: US 8,758,302 B2
(45) Date of Patent: Jun. 24, 2014

(54) HEMOSTATIC VALVE AND SPLITTABLE INTRODUCER

(75) Inventor: Arman H. Valaie, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 292 days.

(21) Appl. No.: 13/142,497

(22) PCT Filed: Dec. 29, 2009

(86) PCT No.: PCT/US2009/069677
§ 371 (c)(1),
(2), (4) Date: Jun. 28, 2011

(87) PCT Pub. No.: WO2010/078317
PCT Pub. Date: Jul. 8, 2010

(65) Prior Publication Data
US 2011/0270196 A1    Nov. 3, 2011

Related U.S. Application Data

(60) Provisional application No. 61/141,272, filed on Dec. 30, 2008.

(51) Int. Cl.
*A61M 5/178*    (2006.01)
*A61M 5/00*    (2006.01)

(52) U.S. Cl.
USPC ............... 604/167.04; 604/167.03; 604/246; 604/247; 604/248; 604/249; 604/256

(58) Field of Classification Search
USPC ............... 604/167.03, 167.04, 246–249, 256; 251/149.1
See application file for complete search history.

(56) References Cited

U.S. PATENT DOCUMENTS

| | | | | |
|---|---|---|---|---|
| 4,626,245 A * | 12/1986 | Weinstein | ............... | 604/167.04 |
| 5,167,637 A * | 12/1992 | Okada et al. | ............ | 604/167.04 |
| 5,385,552 A * | 1/1995 | Haber et al. | ............ | 604/167.03 |
| 8,366,684 B2 * | 2/2013 | Harding | ................... | 604/246 |
| 2007/0123825 A1 * | 5/2007 | King et al. | ................... | 604/160 |

FOREIGN PATENT DOCUMENTS

EP        0308815 A2    3/1989
WO    WO 2004/112865 A2    12/2004

* cited by examiner

*Primary Examiner* — Emily Schmidt
*Assistant Examiner* — Lauren M Peng
(74) *Attorney, Agent, or Firm* — Brinks Gilson & Lione

(57) ABSTRACT

In at least one embodiment, a hemostatic valve for use with a splittable introducer (10) is provided. The hemostatic valve (22) comprises a seal (24) molded in a first configuration of polymeric material and having two adjacent end surfaces (34,35). The seal is deformable from the first configuration into a second configuration. In the first configuration, the seal is substantially non-planer with the two adjacent end surfaces exposed. In the second configuration, the two adjacent end surfaces are unexposed so as to form a split extending through the seal.

11 Claims, 3 Drawing Sheets

HEMOSTATIC VALVE AND SPLITTABLE INTRODUCER

CROSS REFERENCE TO RELATED APPLICATIONS

This application is related to and claims the benefit of priority to PCT/US2009/069677 filed Dec. 29, 2009 which claims the benefit of U.S. provisional patent application 61/141,272 filed on Dec. 30, 2008 entitled "HEMOSTATIC VALVE AND SPLITTABLE INTRODUCER" the entire contents of which are herein incorporated by reference.

BACKGROUND OF THE INVENTION

1. Field of the Invention

The present invention relates generally to medical devices and more specifically, to a splittable introducer having a hemostatic valve system for use in inserting a medical device into a body vessel.

2. Background

Numerous procedures have been developed in modern medicine requiring the percutaneous insertion of one or more medical devices into the vascular system of a patient. Such procedures include, for example, percutaneous transluminal coronary angioplasty (PTCA), X-ray angiographic procedures, and the alike.

The medical devices intended for use in such procedures may be introduced into the vascular system by a variety of known techniques. One widely-used technique is the Seldinger technique. In the Seldinger technique, a surgical opening is made in an artery or vein by a needle, and a guide wire is inserted into the artery or vein through a bore in the needle. The needle is thereafter withdrawn, leaving the guide wire in place. A dilator which is positioned within the lumen of the introducer device is then advanced over the guide wire into the artery or vein. Once the introducer is properly positioned within the artery or vein, the dilator is withdrawn. The introducer may then be used to insert therethrough a variety of medical interventional devices, such as for example, catheters, cardiac leads, and the alike.

One type of introducer is a splittable introducer (also referred to as a peelable introducer, peelable sheath or peel-away sheath). A splittable introducer is used to introduce a medical device, such as a catheter, into a patient and can be subsequently peeled off or away from the medical device to free the medical device from the introducer. One problem with a splittable introducer, however, is that once its sheath is inserted, and the dilator and guide wire have been removed, the sheath provides a passage for the flow of blood. Uncontrolled blood loss through the sheath can have a negative effect on the patient. Another problem with a splittable introducer is that its sheath allows for the introduction of air into the body vessel of the patient. If air is inadvertently introduced into the patient's vein, an air embolism may result with negative effects.

Accordingly, further improvements and enhancements are needed for a splittable introducer, which provides an efficient seal and avoids at least some of the problems encountered with current splittable introducers.

BRIEF SUMMARY OF THE INVENTION

In satisfying the above need and overcoming the above and other drawbacks and limitations of the known technology, the present invention provides a hemostatic valve for use with a splittable introducer. The hemostatic valve comprises a seal molded in a first configuration of polymeric material. The seal has two adjacent end surfaces and is deformable from the first configuration into a second configuration. In the first configuration, the seal is substantially non-planer with the two adjacent end surfaces exposed. In the second configuration, the two adjacent end surfaces are unexposed so as to form a split extending through the seal.

In at least one other embodiment of the present invention, a splittable introducer for use in inserting a medical device into the body of a patient is provided. The splittable introducer comprises the hemostatic valve as discussed in the foregoing paragraph. A splittable hub has an opening formed therethrough. A splittable sheath defines a conduit and extends distally from the opening for insertion into the body of the patient. The hemostatic valve interfaces with the splittable hub to provide access for inserting the medical device through the sheath while obstructing body fluid from flowing out of the opening. The seal is deformed from the first configuration into the second configuration to cover the opening of the splittable hub.

In at least one other embodiment of the present invention, a method for making a hemostatic valve for use with a splittable introducer is provided. The method comprises molding polymeric material to form a seal that has two adjacent end surfaces and is in a first configuration. The seal in the first configuration is substantially non-planer with the two adjacent end surfaces being exposed. The seal is deformed into a second configuration. The seal in the second configuration includes the two adjacent end surfaces being unexposed so as to form a split extending through the seal.

Further objects, features and advantages of the invention will become apparent from consideration of the following description and the appended claims when taken in connection with the accompanying drawings.

DETAILED DESCRIPTION OF THE INVENTION

Detailed embodiments of the present invention are disclosed herein. It is understood however, that the disclosed embodiments are merely exemplary of the invention and may be embodied in various and alternative forms. The figures are not necessarily to scale; some figures may be configured to show the details of a particular component. Therefore, specific structural and functional details disclosed herein are not to be interpreted as limiting but merely as a representative basis for the claims and for teaching one skilled in the art to practice the present invention.

The present invention seeks to overcome some of the problems associated with inserting a medical device into a body channel of a patient via a splittable introducer while providing for substantially leak-free passage of the medical device through the introducer and separation of the splittable introducer from the medical device once inserted.

Employing the principles of the present invention is, for example, a hemostatic valve, a method for making the hemostatic valve, and a splittable introducer which utilizes the hemostatic valve. The hemostatic valve includes a seal that is molded in a first configuration and has two adjacent end surfaces. In the first configuration, the two adjacent end surfaces are exposed and the mold directly interfaces with the two adjacent end surfaces. In one example, the mold forms the two adjacent end surfaces with features that are configured to enhance sealing. The seal is deformed into a second configuration for interfacing with the splittable introducer. In the second configuration, the two adjacent end surfaces are unexposed, e.g., covering each other, to form a split. Preferably, the features on the two adjacent end surfaces interface with each other to enhancing sealing of the splittable introducer. The split is configured to allow a medical device to be advanced through the seal, and to be opened for separating the seal from the medical device.

Figure 1:
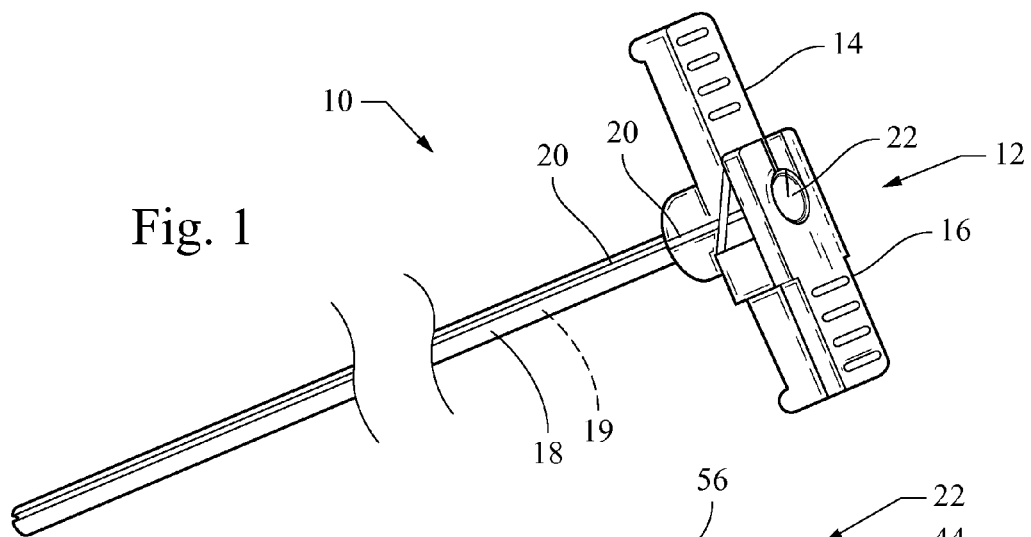
FIG. 1 is a perspective view of a splittable introducer in accordance with an embodiment of the present invention.

Referring to FIG. 1, a splittable introducer in accordance with at least one embodiment of the present invention is provided. The splittable introducer 10 includes a hub 12. The hub 12 comprises a main body 14 and a holding member 16 that holds a hemostatic valve 22. Hard plastic or other suitably rigid and bio-compatible material may be used to form the main body 14 and the holding member 16. The main body 14 and the holding member 16 may be joined together fixedly or may be slidably engaged to allow the holding member 16 to be selectively positioned along the main body 14.

Figure 3:
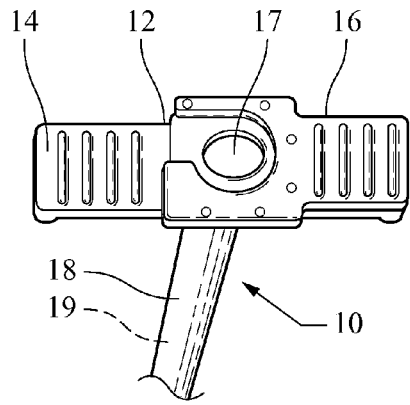
FIG. 3 is a partial perspective view of a splittable introducer in accordance with one embodiment of the present invention.
Figure 4:
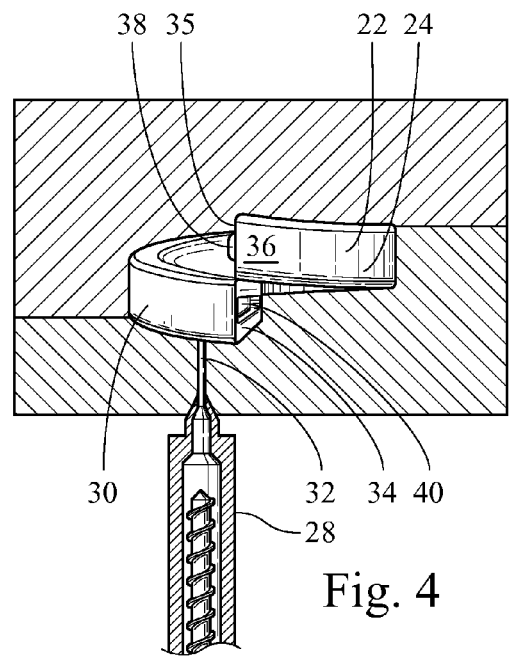
FIG. 4 is a side view a hemostatic valve in a mold in accordance with an embodiment of the present invention.

Referring to FIGS. 1 and 3, the hub 12 has an opening 17 extending through both the main body 14 and the holding member 16. The hemostatic valve 22 is positioned by the holding member 16 to cover the opening 17 and seal the introducer 10. A sheath 18, which may be removable, extends distally from the opening 17 of the hub 12 in a conventional fashion and is for being inserted into a body channel, e.g., body vessel, or cavity of a patient. The sheath 18 is preferably made of a flexible, biocompatible material and defines a conduit 19 for advancing a medical device therein for introduction to and retrieval from the body vessel. The medical device may be a catheter for example, or may be one or more medical devices advanced to and from the body channel over a guide wire as is well known in the art.

The hub 12 and the sheath 18 are each configured to be split or peeled apart. For example, the hub 12 and the sheath 18 may be peeled away from an elongated medical device that is inserted into a patient's body and is also disposed through the hemostatic valve 22, the opening 17 and the conduit 19. In one embodiment, the hub 12 and the sheath 18 each have at least one score line 20, which is in the form of a groove or other frangible feature. Preferably, the score lines 20 of the hub 12 and sheath 18 are longitudinally aligned to facilitate peeling via a slitter (not shown) or other device. In particular, the slitter is advanced along the score lines 20 to generate a concentrated stress at the score lines 20 for peeling apart or splitting open the hub 12 and the sheath 18 and thus, allowing the hub 12 and the sheath 18 to be separated from the medical device.

Referring also to FIGS. 2A-2C and 4, the hemostatic valve 22 includes a seal 24 that is molded of polymeric material in a mold 26. Preferably, the polymeric material is compliant, e.g., elastomeric and soft with a Shore A hardness (durometer) between about 20-100 and is resistant to body fluid for suitable sealing characteristics. For example, the polymeric material may be silicone, polyurethane (PU), thermoplastic elastomer (TPE), copolyester (TEEE), thermoplastic urethane (TPU), thermoplastic vulcanizates (TPV), thermoplastic olefin (TPO), styrenics (e.g. SBC, SBS, SIS, SEBS or SEPS), thermoset and/or vulcanized elastomer, polyvinyl chloride (PVC) or any other suitable elastomeric and/or seal material known to those skilled in the art.

In one embodiment, the mold 26 interfaces with an injection molding machine 28 which is configured to deliver molten (or otherwise liquid) polymeric material into the cavity 30 of the mold 26 via a runner/gate arrangement 32 formed in the mold 26. Once the polymeric material fills the cavity 30, the mold 26 facilitates cooling and/or curing of the polymeric material to form the solid structure of the seal 24 corresponding to the shape of the cavity 30.

Within the mold 26, the seal 24 is formed having two adjacent end surfaces 34 and 35 and is configured substantially non-planer such that the two adjacent end surfaces 34 and 35 are exposed to interior mold surfaces that define at least a portion of the cavity 30. In one embodiment, the seal 24 in the "as molded" configuration 36 corresponds to a helical shape (shown in FIG. 4). In another embodiment, the interior mold surfaces are configured to form corresponding features in the adjacent end surfaces 34 and 35 including a positive feature 38 and a negative feature 40. The negative feature 40 is configured to receive the positive feature 38 (as will be discussed in further detail below).

The seal 24 is deformed from the "as molded" configuration 36 into a "sealing" configuration 42 (shown in FIGS. 2A-2C) for positioning in the holding member 16. In particular, the seal 24 is nominally or negligible stressed in the "as molded" configuration 36, and force is applied to the seal 24 to deform the seal 24 into the "sealing" configuration 42. Also, since the strain (e.g. percent elongation) of a material is related to its stress level (e.g. force per unit area) by the material's modulus (e.g. stress/strain), the seal 24 is also nominally strained in the "as molded" configuration 36 with increased strain (e.g. increased percent elongation) in the "sealing" configuration 42. Nominally strained hereinafter is understood to mean negligibly, insignificantly and/or minimally elongated. That is, the percent elongation of the material is near zero. In one embodiment, the increased strain of the seal 24 in the "sealing" configuration is within the elastic range of the polymeric material and accordingly, the seal 24 is not permanently deformed in the "sealing" configuration 42. The holding member 16 facilitates restraining the seal 24 in the "sealing" configuration 42.

Figure 2A:
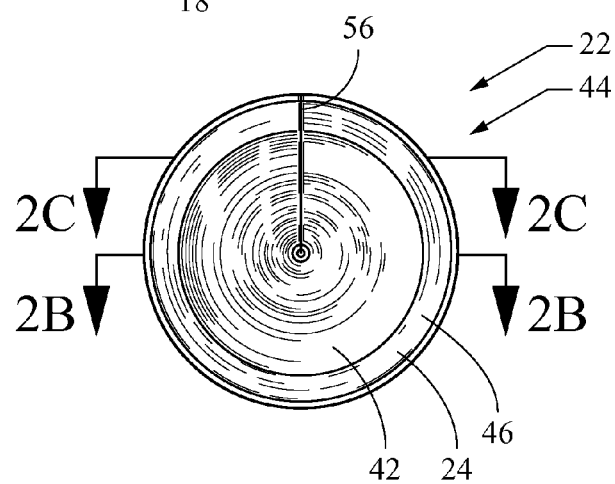
FIG. 2A is a plan view of a hemostatic valve used in a splittable introducer in accordance with one embodiment of the present invention.
Figure 2B:
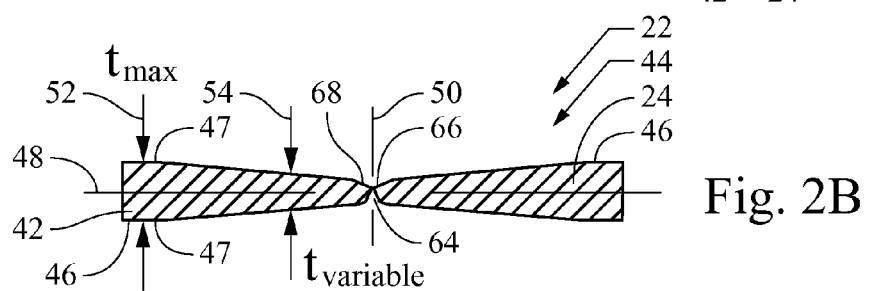
FIG. 2B is a sectional view of the hemostatic valve depicted in FIG. 2A.
Figure 2C:
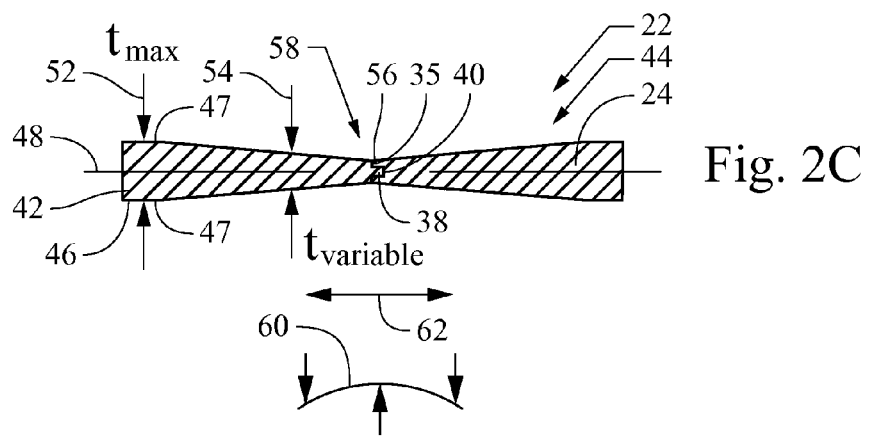
FIG. 2C is a sectional view of the hemostatic valve depicted in FIG. 2A.

In at least one embodiment, the seal 24 in the "sealing" configuration 42 has a diaphragm form 44 (e.g. disk form as illustrated in FIGS. 2A-2C) with an outer perimeter portion 46. The diaphragm form 44 defines a plane 48 extending through the diaphragm form 44 and a central axis 50 positioned at the center of the diaphragm form 44 normal to the plane 48. The outer perimeter portion 46 has two opposing flat surfaces 47 that are substantially parallel and define a maximum thickness 52 of the seal 24. The outer perimeter portion 46 interfaces with the holding member 16 which clamps down and compresses the opposing surfaces 47 to deform and restrain the seal 24 in the "sealing" configuration 42.

In one embodiment, the diaphragm form 44 also has a variable thickness 54 that tapers from the outer perimeter portion 46 to about the central axis 50. The inwardly tapering variable thickness 54 of the seal 24 reduces drag forces and effort for advancing a medical device through the seal 24 and also, reduces pressure on the advancing medical device which may be advantageous for many delicate medical devices.

The two adjacent end surfaces 34 and 35 are unexposed, e.g., cover each other, in the "sealing" configuration 42 to form a split 56 that extends through the seal 24. In one embodiment, the split 56 extends outwardly from about the central axis 50 to the outer perimeter portion 46. That is, the disk form of the seal 24 is split through its thickness 52 and 54 from about its central axis 50 to its outermost perimeter. The split 56 facilitates advancing a medical device through the seal 24, e.g., providing drag force and pressure relief by partial opening of the split 56, and allows the seal 24 to be peeled away from the medical device when the supporting hub 12 is broken away and the split 56 is opened.

As shown in FIG. 2C, the positive feature 38 is received by the negative feature 40. Here the features 38 and 40 are illustrated as a tongue and groove arrangement 58. In one embodiment, this arrangement 58 facilitates retaining and/or restraining the seal 24 in the "sealing" configuration 42 by reinforcing the seal in a shear and/or bending mode 60 while facilitating opening of the seal 24 in a tensile mode 62 for removal from the medical device. Moreover, it is believed that by reinforcing the split 56 in a shear and/or bending mode 60, the seal 24 will have reduced-leakage or be leak-free because the split 56 will be more resistant to opening by bending of the seal 24 caused from body fluid pressure.

Figure 5:
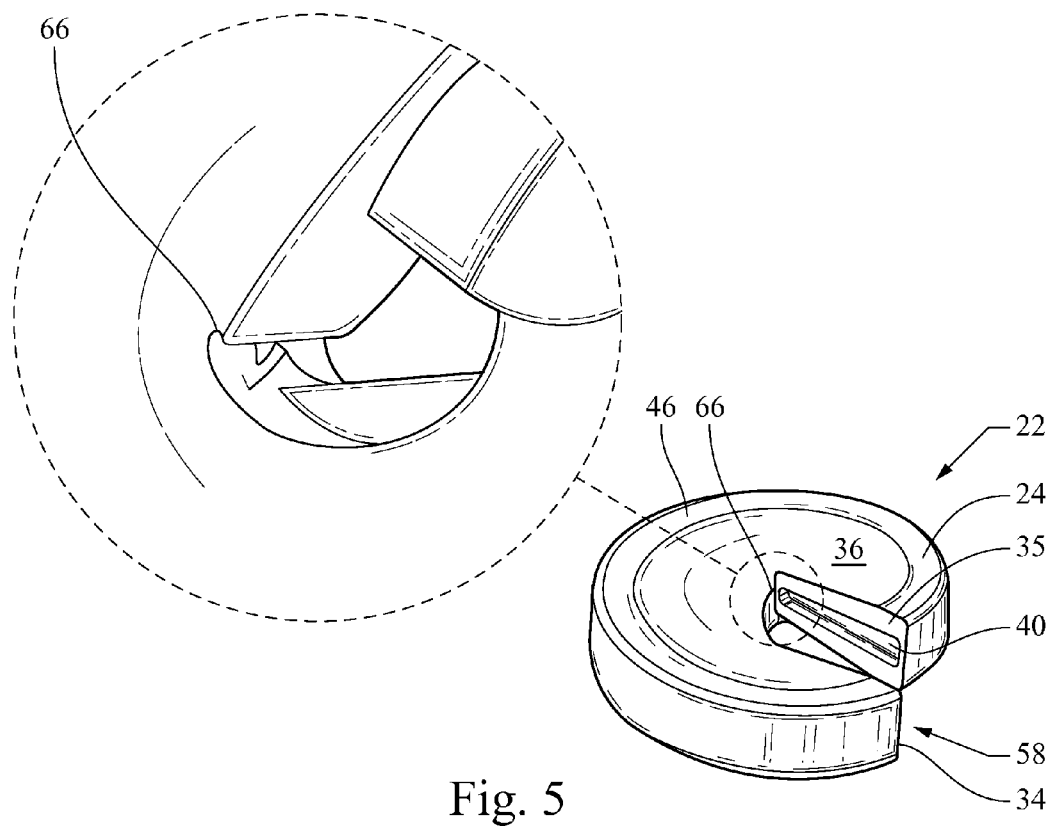
FIG. 5 is a perspective view of the hemostatic valve in accordance with an embodiment of the present invention.

As shown in FIG. 2B, the seal 24 in the "sealing" configuration 42 has a hole 64 extending along the central axis 50. Covering the hole 64 is a spiral lip 66 that is disposed about the central axis 50. FIG. 5 illustrates an enlarged view of the spiral lip 66 when the seal 24 is in the "as molded" configuration 36. In one embodiment, the spiral lip 66 forms a dimple 68 in the outer surface of the seal 24 that facilitates positioning and receiving a medical device relative to the covered hole 64. Moreover, the hole 64 and the reduced thickness of the dimple 68 help to reduce pressure on the medical device while the medical device is being advanced through the seal 24.

Figure 6:
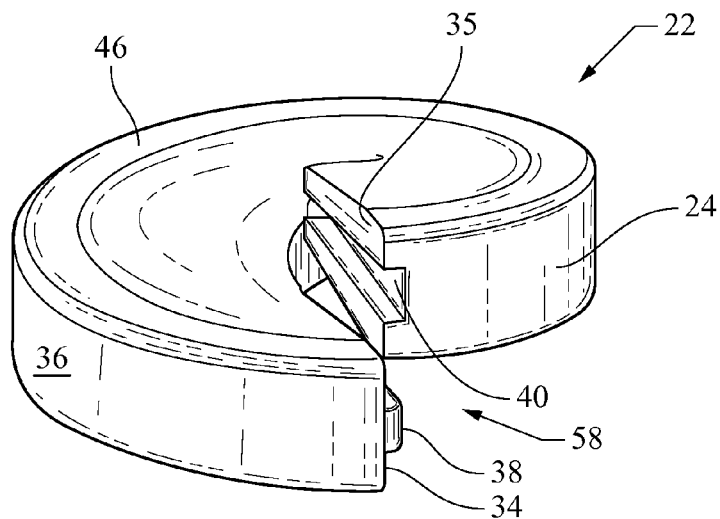
FIG. 6 is a perspective view of the hemostatic valve in accordance with one embodiment of the present invention.

Referring to FIGS. 5 and 6, the positive and negative features 38 and 40 of the tongue and groove arrangement 58 may extend along a partial radial length of the adjacent end surfaces 34 and 35 (FIG. 5). Alternatively, the positive and negative features 38 and 40 may extend along the entire radial length of the adjacent end surfaces 34 and 35.

Figure 7:
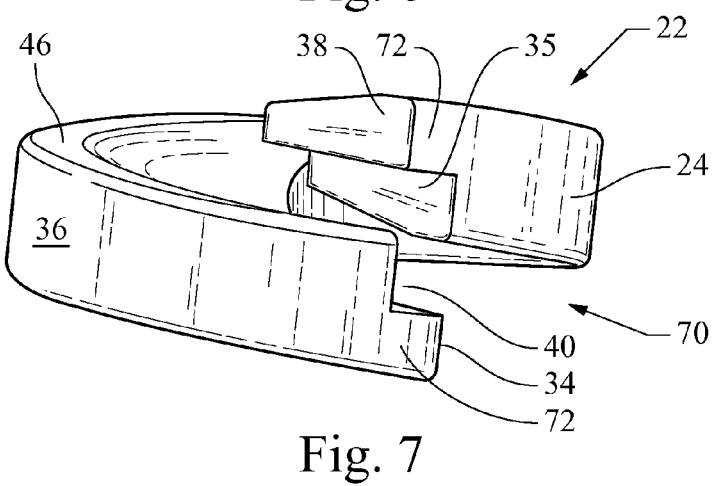
FIG. 7 is a perspective view of a hemostatic valve in accordance with another embodiment of the present invention.

Referring to FIG. 7, an alternative embodiment for the positive and negative features 38 and 40 is provided. Here, the positive and negative features 38 and 40 are configured in a half lap arrangement 70. In the half lap arrangement 70, the positive feature 38 and negative features are formed to create overlapping members 72 which overlap each other when the seal 24 is in the "sealing" configuration 42. In one example, the combined thicknesses of the overlapping members 72 substantially match the thicknesses 52 and 54 of the seal 24 at corresponding radially positions.

Figure 8:
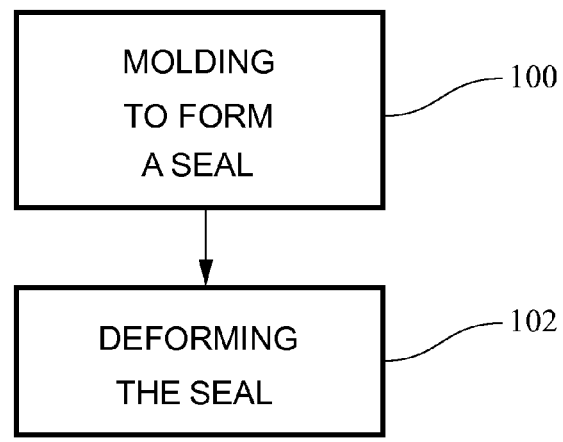
FIG. 8 is an example of a method for making a hemostatic valve in accordance with an embodiment of the present invention.

Referring to FIG. 8, a method for making a hemostatic valve for use with a splittable introducer is provided. The method comprises molding polymeric material to form a seal at 100. The seal has two adjacent end surfaces and is in a first configuration. The seal in the first configuration is substantially non-planer and the two adjacent end surfaces are exposed. The seal is deformed into a second configuration at 102. The seal in the second configuration includes the two adjacent end surfaces unexposed so as to form a slit extending through the seal.

As a person skilled in the art will readily appreciate, the above description is meant as an illustration of the implementation of the principles of the invention. This description is not intended to limit the scope of application of this invention in that the invention is susceptible to modification, variation, and change, without departing from the spirit of this invention as defined in the following claims.

The invention claimed is:

1. A hemostatic valve for use with a splittable introducer, the hemostatic valve comprising:
    a seal formed as a single piece and molded in a first configuration of polymeric material and having two adjacent end surfaces, the seal being deformable from the first configuration into a second configuration, the seal in the first configuration is substantially non-planar with the two adjacent end surfaces exposed and the seal in the second configuration includes the two adjacent end surfaces being unexposed so as to form a split extending through the seal;
    wherein the seal in the second configuration has a diaphragm form with an outer perimeter portion, the diaphragm form defining a plane extending therethrough and a central axis positioned at the center of the diaphragm form normal to the plane;
    wherein the seal in the second configuration has a center hole extending along the central axis and a spiral lip disposed about the central axis covering the center hole, the spiral lip and the hole cooperatively configured to facilitate receiving the medical device; and
    wherein one of the two adjacent end surfaces defines a positive feature and the other of the two adjacent end surfaces defines a negative feature that receives the positive feature when the seal is in the second configuration to enhance sealing of the hemostatic valve.

2. The hemostatic valve according to claim 1 wherein the first configuration corresponds to a helical shape and the second configuration corresponds to a disk shape.

3. The hemostatic valve according to claim 1 wherein the positive and negative features extend along the split when the seal is in the second configuration.

4. The hemostatic valve according to claim 1 the diaphragm form has a maximum thickness at the outer perimeter portion and a variable thickness that is configured to taper from the outer perimeter portion to about the central axis.

5. The hemostatic valve according to claim 4 wherein the outer perimeter portion has two opposing flat surfaces that are substantially parallel and define the maximum thickness.

6. The hemostatic valve according to claim 4 wherein the split extends from about the central axis to the outer perimeter portion to facilitate advancing a medical device through the seal along the central axis and to allow the seal to be peeled away from the medical device by opening the split.

7. A splittable introducer for use in inserting a medical device into a body of a patient that contains body fluid, the introducer comprising:
    a splittable hub having an opening formed therethrough;
    a splittable sheath defining a conduit and extending distally from the opening for insertion into the body of the patient; and
    a hemostatic valve interfacing with the splittable hub to provide access for inserting the medical device through the sheath while obstructing the body fluid from flowing out of the opening, the hemostatic valve comprising:

a seal formed as a single piece and molded in a first configuration of polymeric material and having two adjacent end surfaces, the seal deformed from the first configuration into a second configuration to cover the opening, the seal in the first configuration is substantially non-planar with the two adjacent end surfaces exposed and the seal in the second configuration includes the two adjacent end surfaces being unexposed so as to form a split extending through the seal;

wherein the seal in the second configuration has a diaphragm form with an outer perimeter portion, the diaphragm form defining a plane extending therethrough and a central axis positioned at the center of the diaphragm form normal to the plane;

wherein the seal in the second configuration has a center hole extending along the central axis and a spiral lip disposed about the central axis covering the center hole, the spiral lip and the hole cooperatively configured to facilitate receiving the medical device; and wherein one of the two adjacent end surfaces defines a positive feature and the other of the two adjacent end surfaces defines a negative feature that receives the positive feature when the seal is in the second configuration to enhance sealing of the hemostatic valve.

8. The splittable introducer according to claim 7 wherein the first configuration corresponds to a helical shape and the second configuration corresponds to a disk shape.

9. The splittable introducer according to claim 7 wherein the diaphragm form has a maximum thickness at the outer perimeter portion and a variable thickness that is configured to taper from the outer perimeter portion to about the central axis.

10. The splittable introducer according to claim 9 wherein the split extends from about the central axis to the outer perimeter portion to facilitate advancing a medical device through the seal along the central axis and to allow the seal to be peeled away from the medical device by opening the split.

11. A method for making a hemostatic valve for use with a splittable introducer, the method comprising:

molding polymeric material to form a seal that has two adjacent end surfaces and is in a first configuration, the seal in the first configuration being substantially non-planar with the two adjacent end surfaces exposed; and deforming the seal into a second configuration, the seal in the second configuration including the two adjacent end surfaces being unexposed so as to form a split extending through the seal;

wherein the seal in the second configuration has a diaphragm form with an outer perimeter portion, the diaphragm form defining a plane extending therethrough and a central axis positioned at the center of the diaphragm form normal to the plane;

wherein the seal in the second configuration has a center hole extending along the central axis and a spiral lip disposed about the central axis covering the center hole, the spiral lip and the hole cooperatively configured to facilitate receiving the medical device; and wherein one of the two adjacent end surfaces defines a positive feature and the other of the two adjacent end surfaces defines a negative feature that receives the positive feature when the seal is in the second configuration to enhance sealing of the hemostatic valve.

\* \* \* \* \*